United States Patent
Becker et al.

(10) Patent No.: US 10,660,599 B2
(45) Date of Patent: May 26, 2020

(54) METHOD AND DEVICE FOR POSITIONING AN EMITTER

(71) Applicant: SIEMENS HEALTHCARE GMBH, Erlangen (DE)

(72) Inventors: Anne-Katrin Becker, Nuremberg (DE); Steffen Benndorf, Roethenbach (DE); Franziska Dinse, Heiligenstadt (DE); Susanne Dornberger, Erlangen (DE); Michael Fuhrmann, Herzogenaurach (DE); Philip Hafner, Zirndorf (DE); Sultan Haider, Erlangen (DE); Ralf Nanke, Neunkirchen am Brand (DE); Sabine Schaeffer-Kundler, Herzogenaurach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 298 days.

(21) Appl. No.: 15/316,594

(22) PCT Filed: Mar. 24, 2015

(86) PCT No.: PCT/EP2015/056291
§ 371 (c)(1),
(2) Date: Dec. 6, 2016

(87) PCT Pub. No.: WO2015/185235
PCT Pub. Date: Dec. 10, 2015

(65) Prior Publication Data
US 2017/0135667 A1 May 18, 2017

(30) Foreign Application Priority Data
Jun. 6, 2014 (DE) .................... 10 2014 210 897

(51) Int. Cl.
*A61B 6/00* (2006.01)

(52) U.S. Cl.
CPC ............ *A61B 6/547* (2013.01); *A61B 6/4411* (2013.01); *A61B 6/4464* (2013.01); *A61B 6/587* (2013.01); *A61B 6/588* (2013.01)

(58) Field of Classification Search
CPC ......... A61B 6/547; A61B 6/587; A61B 6/588; A61B 6/4411
See application file for complete search history.

(56) References Cited

U.S. PATENT DOCUMENTS 6,447,163 B1 * 9/2002 Bani-Hashemi ......... A61B 6/08
378/205
6,461,040 B1 * 10/2002 Mattson ................... A61B 6/08
378/205

(Continued)

FOREIGN PATENT DOCUMENTS

DE 8502255 U1 5/1985
DE 10216857 A1 11/2003
(Continued)

*Primary Examiner* — David J Makiya
*Assistant Examiner* — Soorena Kefayati
(74) *Attorney, Agent, or Firm* — Laurence Greenberg; Werner Stemer; Ralph Locher (57) ABSTRACT

A method for positioning an emitter relative to a detector includes determining the position of the detector relative to the emitter, changing the position of the detector and measuring the change in position using a measuring device located in the detector. Data related to the change in position of the detector is then supplied to a device for positioning the emitter, and the position of the emitter is changed in accordance with the data. An image capture device is also provided.

11 Claims, 5 Drawing Sheets

(56) References Cited

U.S. PATENT DOCUMENTS

| | | |
|---|---|---|
| 6,859,521 B2 | 2/2005 | Spahn |
| 7,156,553 B2 | 1/2007 | Tanaka et al. |
| 8,232,859 B2 | 7/2012 | Hou et al. |
| 8,690,426 B2* | 4/2014 | Liu ................... G03B 42/02 250/370.09 |
| 8,696,200 B2* | 4/2014 | Mohr ................... A61B 6/08 378/196 |
| 2002/0150215 A1* | 10/2002 | Barnes ................ A61B 6/4405 378/197 |
| 2003/0194056 A1* | 10/2003 | Spahn ................. A61B 6/08 378/205 |
| 2006/0109958 A1* | 5/2006 | Ertel ................... A61B 6/08 378/205 |
| 2007/0086570 A1* | 4/2007 | Spahn ................. A61B 6/102 378/117 |
| 2007/0165775 A1* | 7/2007 | Graumann ........... A61B 6/4441 378/19 |
| 2008/0130836 A1* | 6/2008 | Graumann ........... A61B 6/06 378/177 |
| 2008/0165933 A1* | 7/2008 | Hornig ................ A61B 6/08 378/206 |
| 2008/0232553 A1* | 9/2008 | Agano ................. A61B 6/4429 378/197 |
| 2009/0086926 A1* | 4/2009 | Wang .................. A61B 6/4405 378/206 |
| 2009/0257564 A1* | 10/2009 | Kito .................... A61B 6/4283 378/206 |
| 2010/0239070 A1* | 9/2010 | Mohr ................... A61B 6/08 378/98 |
| 2011/0013752 A1* | 1/2011 | Takahashi ........... A61B 6/583 378/205 |
| 2011/0069812 A1* | 3/2011 | Takahashi ........... A61B 6/025 378/21 |
| 2011/0075817 A1* | 3/2011 | Takahashi ........... G03B 42/04 378/189 |
| 2011/0164721 A1* | 7/2011 | Jank .................... A61B 6/4441 378/4 |
| 2011/0199298 A1 | 8/2011 | Bassompiere et al. |
| 2011/0249791 A1* | 10/2011 | Wang .................. A61B 6/08 378/62 |
| 2011/0249799 A1* | 10/2011 | Lalena ................ A61B 6/08 378/97 |
| 2011/0254922 A1* | 10/2011 | Schaerer ............. A61B 90/90 348/46 |
| 2011/0288805 A1 | 11/2011 | Dejnabadi et al. |
| 2014/0050306 A1* | 2/2014 | Mu ...................... A61B 6/547 |
| 2014/0133627 A1* | 5/2014 | Sakuragi ............. A61B 6/4429 378/62 |
| 2014/0247918 A1* | 9/2014 | Kang .................. A61B 6/4405 378/62 |
| 2014/0314204 A1* | 10/2014 | Sabczynski ......... A61B 6/08 378/62 |
| 2014/0376700 A1* | 12/2014 | Kwak .................. A61B 6/4291 378/205 |
| 2015/0098551 A1* | 4/2015 | Kwak .................. A61B 6/548 378/91 |
| 2015/0190104 A1* | 7/2015 | Exelmans ............ A61B 6/4452 378/62 |
| 2016/0143609 A1* | 5/2016 | Park .................... A61B 6/547 378/98.2 |
| 2016/0183909 A1* | 6/2016 | Mehendale ......... A61B 6/08 378/205 |
| 2017/0332986 A1* | 11/2017 | Grondin .............. A61B 6/588 |

FOREIGN PATENT DOCUMENTS

| | | |
|---|---|---|
| DE | 102009013572 A1 | 9/2010 |
| DE | 102010008552 A1 | 8/2011 |
| DE | 112010003260 T5 | 1/2013 |
| DE | 102009013572 B4 | 2/2013 |
| EP | 2700361 A1 | 2/2014 |
| JP | 2002143139 A | 5/2002 |

* cited by examiner

METHOD AND DEVICE FOR POSITIONING AN EMITTER

BACKGROUND OF THE INVENTION

Field of the Invention

The invention relates to a method and a device for positioning an emitter relative to a detector.

In radiology, the attenuation of x-rays as they pass through objects is exploited in order to draw conclusions concerning properties of the irradiated tissue (the density is usually determined). Two central components of every radiology installation are the X-ray emitter (or the X-ray source) and the X-ray detector. For the purpose of taking X-rays, both components are oriented relative to each other in such a way that the X-rays emitted by the X-ray emitter can be detected by the detector. There are a number of radiology systems that have various degrees of freedom with respect to the positioning of X-ray emitter and X-ray detector, in order thereby to permit different types of examinations and to allow adaptations to the anatomy of the particular patient. If X-ray emitter and X-ray detector can be moved independently, i.e. are not connected rigidly to each other as in the case of the C-arc or the computed tomography apparatus for example, the optimal positioning of these two components for the particular examination is a complex task. Moreover, account has to be taken of efficiency demands, i.e. the positioning of emitter and detector should take place as quickly as possible in order to permit an efficient workflow.

For the positioning of X-ray emitter and X-ray detector, the document DE 10216857 A1 has proposed providing these with markers which are optically identified by CCD cameras positioned in the examination room. The positioning then takes place with the aid of these markers recorded by CCD cameras. However, this solution has the disadvantage that objects located between the components and the CCD cameras may obstruct a correct detection of the markers. A situation of this kind may arise, for example, in so-called over-table apparatuses in which the detector is typically positioned directly underneath the patient table and, consequently, the patient table may constitute an obstacle to the detection of markers. Moreover, the stated solution requires that CCD cameras (sometimes a large number of them because of the stated problems) are arranged in the treatment room, which entails not inconsiderable expense.

BRIEF SUMMARY OF THE INVENTION

The object of the invention is to achieve inexpensive and efficient positioning of an emitter.

This object is achieved by a method as described below and by an image capture device as described below.

According to the invention, an emitter is positioned relative to a detector (typically in such a way that emitter and detector can interact for capturing an image of an object). First of all, the position of the detector relative to the emitter is determined. In addition to determining the relative position, it is also possible to determine the orientation of the detector (preferably with respect to an axis of symmetry of the emitter). For the determination of relative position and orientation, at least one marker (e.g. an optical marker) can be provided on the detector, and at least one sensor (e.g. a camera) for the detection of the at least one marker can be provided on the emitter. This initial step is also referred to below as registration (of the emitter with respect to the detector).

A change in the position of the detector takes place after the registration. Typically, the detector is brought to a position in which an image can be captured (e.g. underneath a patient table). Before the change in position, it is possible, according to one embodiment, to adapt the orientation of the detector in accordance with the deviation from a desired orientation (the e.g. orientation by means of emitters corresponding to markers in the course of the registration), such that the orientation no longer has to be adapted after the change in position of the detector. During the change in position of the detector, the change in position (and possibly also a change in the orientation of the detector) is measured or determined using a measuring means arranged in the detector. Here, "arranged in the detector" signifies that the measuring means is rigidly connected to the detector and is moved with it, i.e. this also includes in particular a mounting (possibly also a releasable mounting) of the measuring means on the detector. The measuring means can be, for example, a gyroscope, an acceleration sensor, a compass, or a combination of the aforementioned means. The measurement of the change in position relates at least to one degree of freedom and preferably all degrees of freedom of the detector.

In the course of the invention, data relating to the change in position (and possibly also to a change in orientation) are supplied to a device for positioning the emitter. These data relate preferably to all the degrees of freedom relevant to the detector. This can be done by (generally wireless) transmission of the data, via a transmitter mounted on the detector, to a control system of the device for positioning the emitter. The receiver for the data transmitted from the emitter can also be arranged separately from the device for positioning the emitter (e.g. on the emitter), and the data can be forwarded from the receiver to the device for positioning. The latter scenario is to be understood as an alternative according to the invention for the transmission of the data.

Finally, a change in the position of the emitter is effected, in accordance with the transmitted data, by the device for positioning the emitter. This can be done during the change in position of the detector, i.e. concurrently as it were, or it can be done subsequently. In the latter case, an addition or integration of transmitted data relating to changes in position of the detector can take place, such that resulting data on the total change in position or orientation of the emitter are present and the emitter is moved accordingly (possibly triggered by being enabled by the operating personnel). The first variant (direct entrainment of the emitter) is more suggestive, whereas, in the second variant, collisions can be better excluded. According to one embodiment of the subject matter of the invention, a desired distance between the emitter and the detector is predefined (e.g. in the sense of an optimized image capture geometry) and the change in the position of the emitter in accordance with the data is carried out in such a way that the distance between emitter and detector corresponds to the desired distance.

According to a development of the subject matter of the invention, the sensor mounted on the emitter is designed to measure the change in position of the detector. Then, for example, the change in position measured by the measuring means arranged in the detector is used for the change in position of the emitter if (possibly only if) (and the measuring means is possibly also only activated in this situation) the sensor mounted on the emitter is not available for measuring the change in position of the detector. This development is expedient in particular if the detection of the change in position can be effected more accurately or more reliably by the sensor mounted on the emitter than by the measuring means arranged in the detector. For example, this can be the case if the sensor mounted on the emitter directly steers the detector. The measuring means arranged in the detector would then come into use if steering by the sensor mounted on the emitter were not possible (or no longer possible) as a result of an object (e.g. patient table) between emitter and detector. In the course of this embodiment, the measuring of the change in position of the detector can be monitored by the sensor mounted on the emitter, and an automatic switch can be made to measurement of the change in position by the measuring means arranged in the detector (or to use of the corresponding measured results), when the sensor mounted on the emitter does not supply any measured results for the change in position of the detector (e.g. because radiation emitted for the measurement cannot propagate without obstruction between emitter and detector on account of an object mounted between them (patient table, accessories, etc.)).

According to a development of the subject matter of the invention, provision is made that, after the change in position of the emitter by means of at least one marker (e.g. an optical marker) mounted on the detector and by means of at least one sensor (e.g. camera) mounted on the emitter for the purpose of detecting the at least one marker, the distance and/or the orientation between emitter and detector is finely adjusted. For this purpose, the detector can contain a deployable element which comprises a marker (e.g. an optically detectable marker) that can be detected by a sensor of the emitter.

The invention also comprises an image capture device with an emitter, a detector, and means for positioning an emitter relative to a detector. This image capture device moreover comprises means for determining the position of the detector relative to the emitter (e.g. marker and detector), means for changing the position of the detector (e.g. a corresponding drive), and measuring means arranged in the detector and used for measuring the change in position. Moreover, the image capture device is provided with means (e.g. transmitter/receiver pairing) for supplying data, which relate to the change in position of the detector, to a device for positioning the emitter, and means (e.g. a drive, and a movable arm on which the emitter is secured) for changing the position of the emitter in accordance with the data.

BRIEF DESCRIPTION OF THE SEVERAL VIEWS OF THE DRAWING

The invention is described in more detail below on the basis of an illustrative embodiment and with reference to figures, in which.

DESCRIPTION OF THE INVENTION

Figure 1:
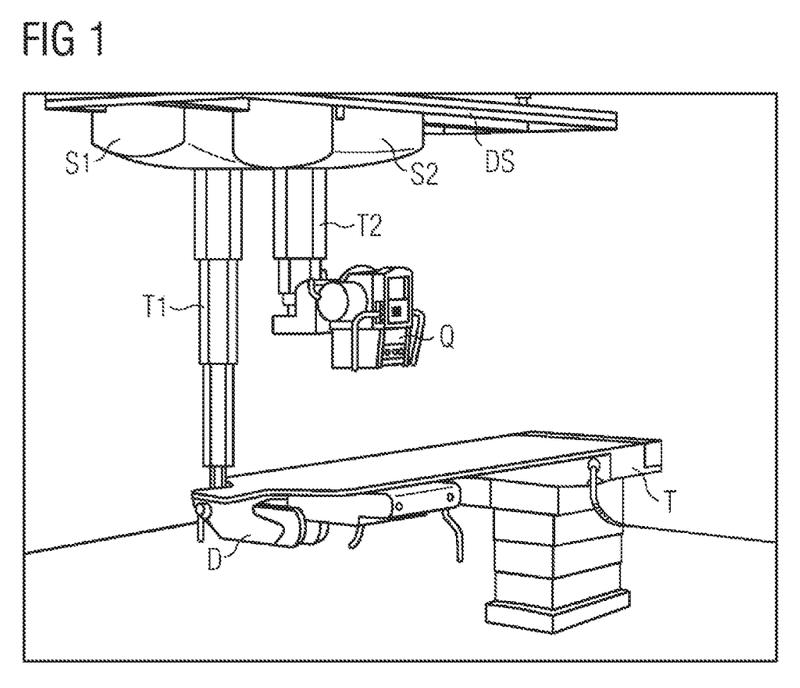
FIG. 1 shows a ceiling mount.

A ceiling mount used for radiography examinations is shown in FIG. 1. Two carriages S1 and S2 are mounted on ceiling rails DS and each carry a telescopic arm T1, T2, respectively. The source Q is secured on telescopic arm T2, and the detector D is secured on telescopic arm T1. The ceiling rails DS each permit a translation in the horizontal direction, while the telescopic arms each permit a translation in the vertical direction. A table T is provided on which a patient is intended to lie. This table can likewise be designed for translation in the horizontal direction. As is shown in the figure, the detector can be positioned underneath the table top. Both the source and the detector are provided with degrees of freedom of tilting which, in interaction with degrees of freedom of rotation, permit any desired angle settings of source and detector.

Figure 2:
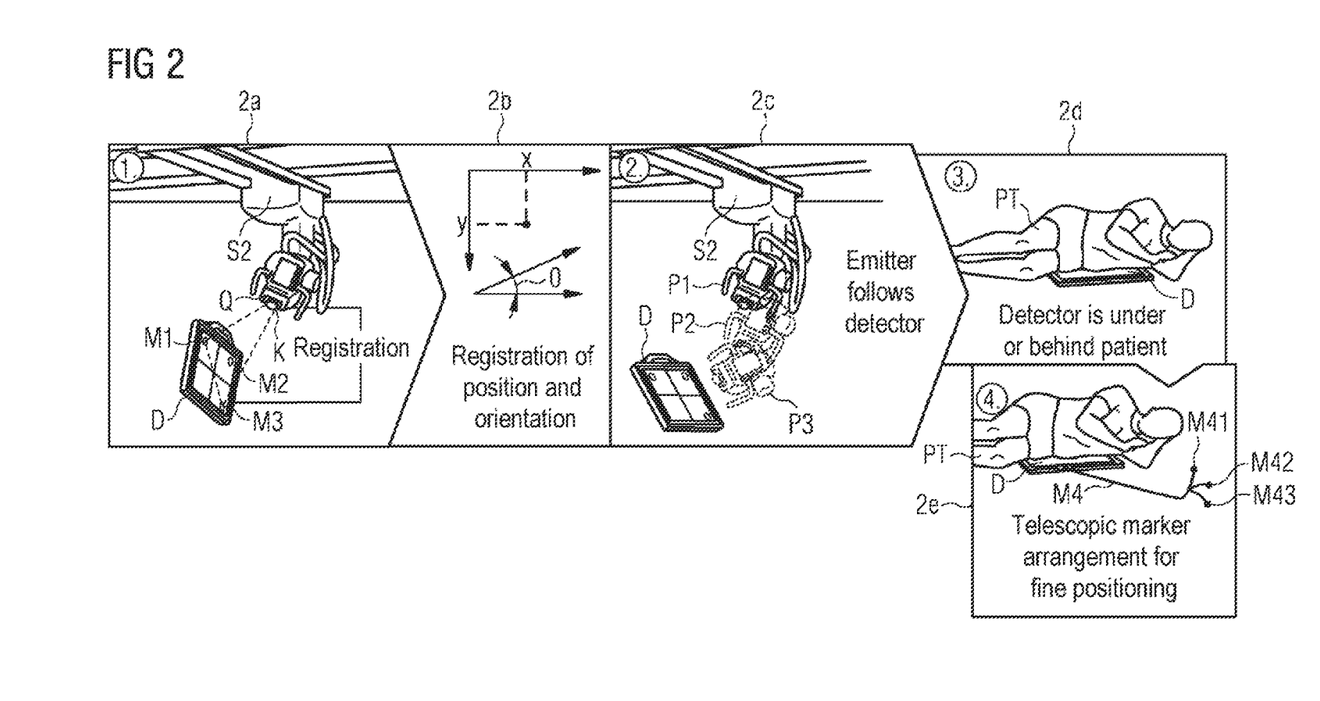
FIG. 2 shows a workflow configured according to the invention.

FIG. 2 is divided into subsidiary FIGS. 2*a*, 2*b*, 2*c*, 2*d* and 2*e*. FIG. 2*a* shows a ceiling mount with a carriage S2 which carries an X-ray source Q. This X-ray source Q is equipped with a camera K. The camera K (e.g. a CCD camera) is designed to detect markers M1, M2, M3 of a detector D. Three markers have been chosen here on account of the fact that they make it possible to determine all of the data on position and orientation of the detector D.

Three degrees of freedom, three for the position and three for the orientation). In other words, three points are sufficient to establish the plane defined by the detector. In a first step, a registration of the detector is carried out with respect to the X-ray source Q, i.e. position and orientation are determined in a system of coordinates used for the source. In the course of the positioning, it is possible to use absolute coordinates and also relative coordinates, or a spatially fixed system of coordinates, or a system of coordinates entrained with the source.

Subsidiary FIG. 2*b* illustrates that position coordinates and angles are established during the registration (in particular the original distance (initial depth) between emitter and detector). The next view, in FIG. 2*c*, shows the source in the three positions P1, P2 and P3 and thus illustrates that the emitter Q follows an executed detector movement. As long as there is visual contact between the source Q and the detector D, the camera K is used for this purpose. However, the camera can no longer be used if the visual contact is lost.

Therefore, the detector D is additionally equipped with a means for calculating the data relevant to its movement (change in position and change in orientation). The detection and analysis of a translational movement can be performed with the aid of a multi-axial acceleration meter, as is also described, for example, in DE 112010003260 T5. Tilting and rotation can be detected using a gyroscope. A gyroscope can be combined with the acceleration sensor in order in this way to be able to determine up to six degrees of freedom (three for rotation and three for translation). This is also disclosed, for example, in the document US 2011/0199298 A1. Elements of this kind can be produced, for example, in what is called micro-electro mechanical systems (MEMS) technology, as is described, for example, in US 20110288805 A1.

Figure 3A:
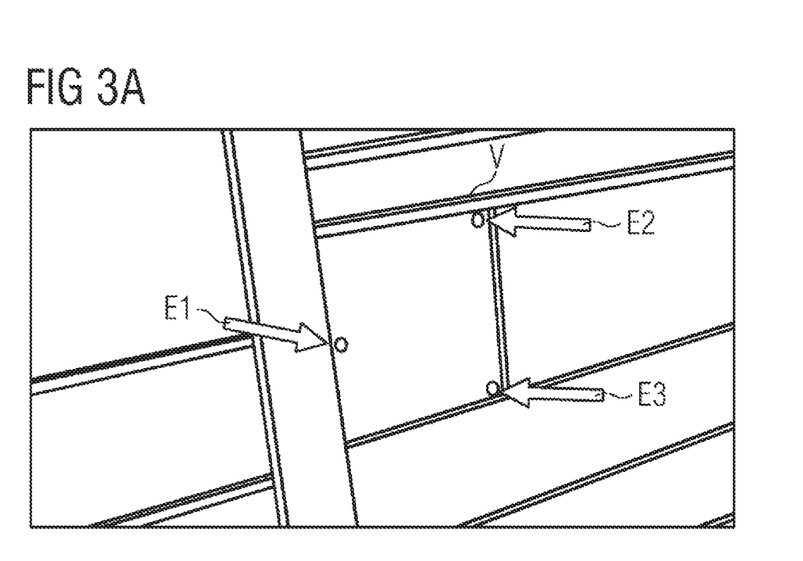
FIG. 3 shows device elements for transmitting data that are determined in the detector and that relate to a change in position of the detector.
Figure 3B:
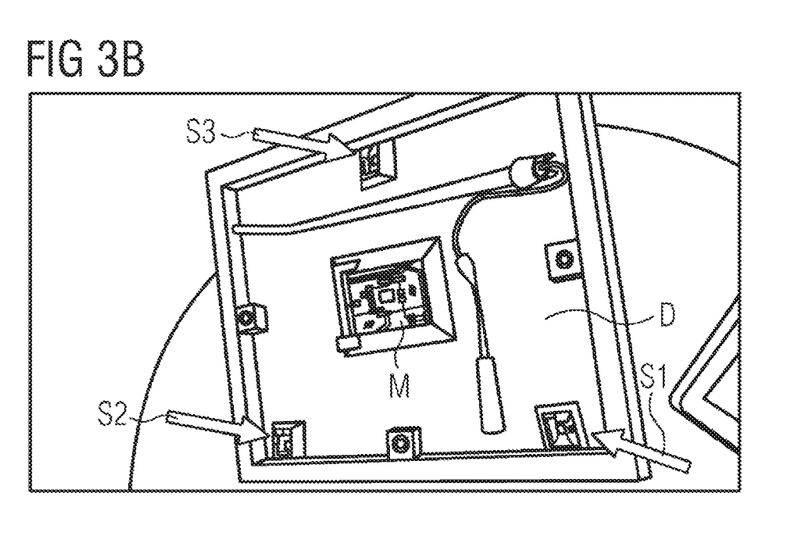

The data detected by measuring means provided for this purpose in the detector D, and relating to the change in position and orientation, are transmitted to the source for tracking thereof. This can be done, for example, wirelessly by means of a transmitter arranged in the detector, wherein the transmitted data are received by a transmitter in contact with the control system of the source Q. FIG. 3 shows, at the top, a detail of a device V for positioning the emitter, which device V is equipped with three receivers E1, E2 and E3 (FIG. 3*a*). In FIG. 3*b* at the bottom, a detector is shown which correspondingly has three transmitters S1, S2 and S3. The data, which were obtained by a measuring means M mounted on the detector, are transmitted with the aid of these receivers E1, E2 and E3 and the transmitters S1, S2 and S3, which transmitters and receivers can also be used selectively according to requirements.

In FIG. 2d, finally, a patient PT is shown in a recumbent position. The detector D is positioned underneath the patient. According to the invention, the emitter Q (not shown in FIG. 2d) follows the detector D and is already arranged basically in an image capture position. For the image capture, a check of the position is additionally carried out and, if appropriate, fine positioning of the source Q. The corresponding procedure is shown in FIG. 2e. The detector D comprises a telescopic marker arrangement M4, which is deployed for the fine positioning. At the end of this marker arrangement M4, three marker points M41, M42 and M43 are arranged such that an optical determination of all the relevant degrees of freedom can be carried out again (the fine positioning can entail all the degrees of freedom or else, for example, can be limited to just the orientation of the detector). After the fine positioning, the marker arrangement M4 can be retracted again and received by the detector D.

Figure 4:
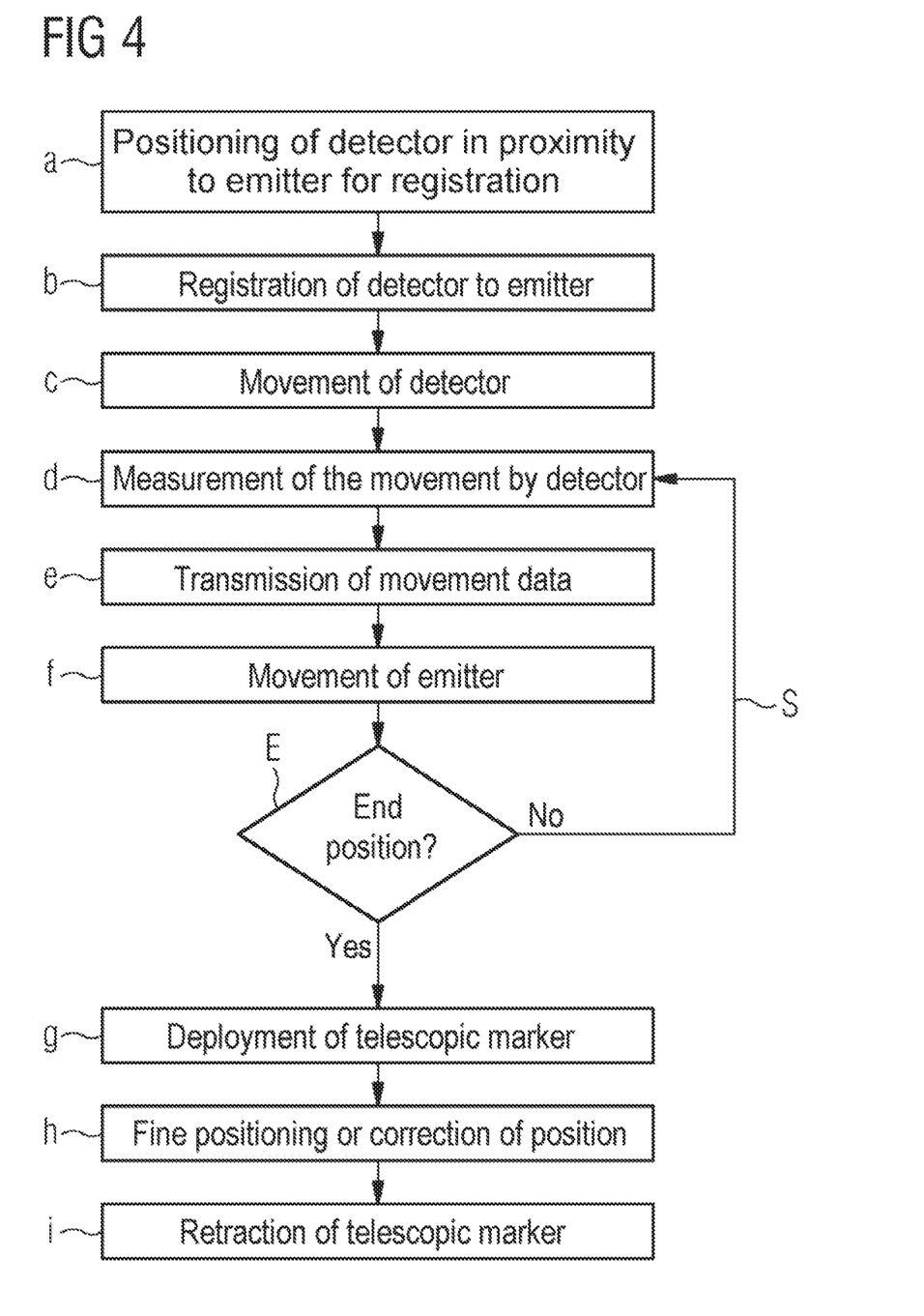
FIG. 4 shows a flow chart of a method according to the invention.

FIG. 4 shows a flow chart of a procedure according to the invention. First, the detector D is positioned in the proximity of the emitter for the registration (step a), and the registration is carried out (step b). This is followed by a simultaneous movement of detector and emitter, wherein the emitter instantaneously tracks the detector movement. During movement of the detector (step c), the executed movement is determined (step d) by measurement by measuring means in the detector, and corresponding movement data are transmitted to the device for moving the emitter (step e). The emitter is then moved accordingly (step f). (If, for example, there is visual contact between emitter and detector, steps d and e can be replaced by a measurement of the movement data by a sensor mounted on the emitter). With suitable precision of discrete steps c to f, the observer or operator is provided, by way of the loop S, with a continuous movement of the emitter, which follows the detector. When the end position is reached (query E—e.g. identification of the end position after expiry of a timer for movement of the detector), the fine positioning or fine correction is carried out. The telescopic marker is deployed (step g), the fine positioning or fine correction is carried out (step h), and the telescopic marker is retracted again (step i).

Figure 5:
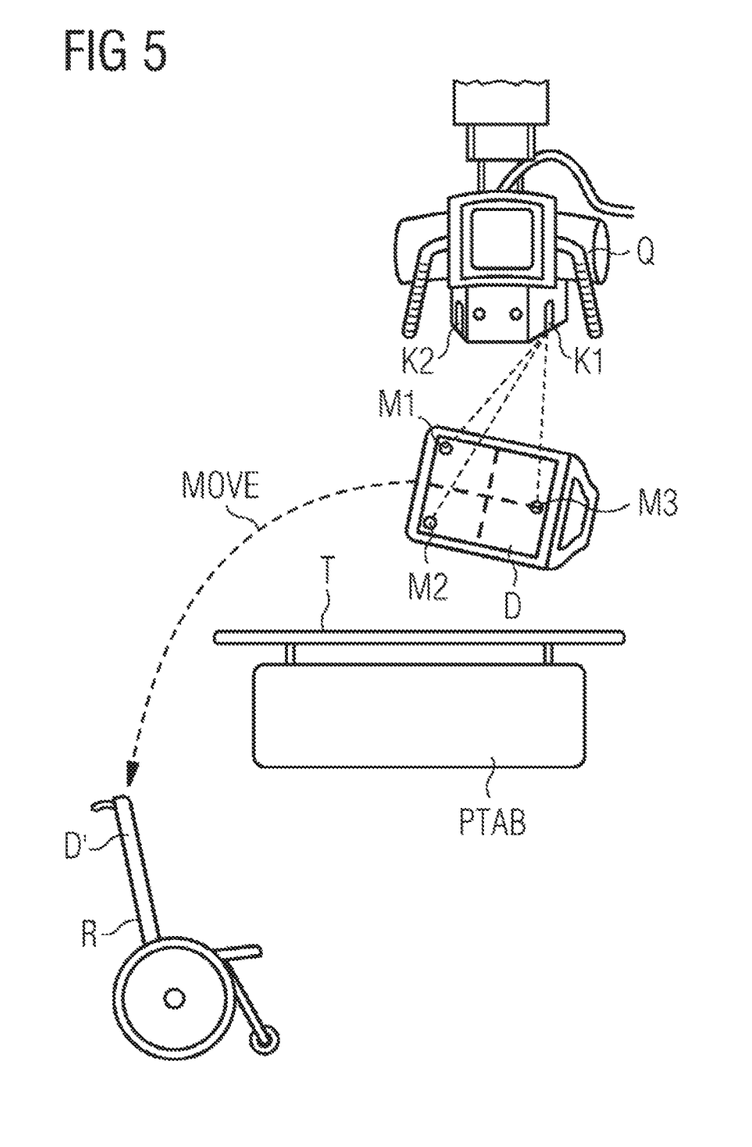
FIG. 5 shows another view of a method according to the invention.

The procedure according to the invention is shown once again in FIG. 5. A source Q is shown which is equipped with two cameras K1 and K2. A detector (e.g. operating wirelessly) is likewise shown which detects the markers M1, M2 and M3. First of all, in a first step, the detector is brought into the proximity of the source Q in such a way that the registration can take place. This is done by identification of the optical markers M1, M2 and M3. The detector is then positioned for image capture. This is illustrated by the line designated by the reference sign MOVE. The source Q follows the detector on the basis of data determined in the detector and relating to the change in position and orientation. This tracking can take place immediately or only after an end position of the detector D has been reached and the operating personnel have then enabled the positioning of the source Q. A wheelchair R is depicted, and the detector is indicated there in its end position D'. After the source Q has carried out the corresponding change in position, it is possible for a fine positioning then to take place, as is shown in FIG. 2e. The figure additionally shows a patient table T, which signifies that the method according to the invention could also be used for the latter, i.e. the preferably wirelessly configured detector D can be flexibly positioned for use at different positions (e.g. wheelchair or patient table).

The invention is not limited to the above illustrative embodiment. A person skilled in the art will be able, as a matter of routine, to identify many other possible uses and design variants that exploit the concept of the invention and that do not depart from the scope of protection of the claims.

The invention claimed is:

1. A method for positioning an emitter relative to a detector, the method comprising the following steps:
   determining a position of the detector relative to the emitter by using at least one marker mounted on the detector and by using at least one camera mounted on the emitter, for detecting the at least one marker;
   changing the position of the detector and measuring a change in position of the detector by using a measuring device disposed in the detector;
   supplying data, relating to the change in position of the detector, to a device for positioning the emitter;
   changing the position of the emitter in accordance with the data;
   determining a change in position of the detector using the at least one camera mounted on the emitter when the at least one camera is in visual contact with said at least one marker and is able to measure the change of position of the detector, otherwise,
   determining the change in position of the detector using the measuring device disposed in the detector when the at least one camera mounted on the emitter loses visual contact with said at least one marker and does not supply any measured results for the change in position of the detector.

2. The method according to claim 1, which further comprises:
   monitoring the measurement of the change in position of the detector using the at least one camera mounted on the emitter; and
   automatically switching to measurement of the change in position by the measuring device disposed in the detector, or to measured results obtained by the measuring device, when the at least one camera mounted on the emitter provides no measured results for the change in position of the detector.

3. The method according to claim 1, which further comprises determining an orientation of the detector in addition to the relative position of the detector.

4. The method according to claim 1, which further comprises measuring a change in an orientation of the detector by using the measuring device disposed in the detector, when the position of the detector is changed.

5. The method according to claim 1, which further comprises predefining a desired distance between the emitter and the detector, and changing the position of the emitter in accordance with the data to cause the distance between the emitter and the detector to correspond to the desired distance.

6. The method according to claim 1, which further comprises finely adjusting at least one of a distance or an orientation between the emitter and the detector after changing the position of the emitter by using the at least one marker mounted on the detector and by using the at least one camera mounted on the emitter for detecting the at least one marker.

7. The method according to claim 3, which further comprises, before changing the position of the detector, adapting the orientation of the detector in accordance with a deviation of the orientation from a desired orientation.

8. The method according to claim 4, wherein said measuring device disposed in the detector includes at least one of a gyroscope, an acceleration sensor, a compass or a combination of a gyroscope, an acceleration sensor and a compass for measuring the change in position or the change in orientation.

9. The method according to claim 4, which further comprises transmitting data relating to the change in position or change in orientation of the detector, from a transmitter mounted on the detector to a control system of the device for positioning the emitter.

10. An image capture device for positioning an emitter relative to a detector, the image capture device comprising:
   an emitter;
   a detector;
   said emitter positionable relative to said detector by an apparatus including:
      at least one camera mounted on said emitter and configured to visually detect at least one marker mounted on said detector and determine a change in position of said detector;
      a first drive configured to change the position of said detector,
      a position sensor arranged in said detector and configured to measure the change in position of said detector, the change in position of said detector measured by said position sensor being used to determine a change in the position of said detector when said at least one camera mounted on said emitter loses visual contact with said at least one marker and does not supply any measured results for the change in position of said detector,
      a transmitter for supplying data relating to the change in position of said detector to a second drive configured to change the position of said emitter, and
      said second drive configured to change the position of said emitter in accordance with the data supplied by said transmitter.

11. The image capture device according to claim 10, wherein said detector contains an extendable element including said at least one marker to be detected by said at least one camera of said emitter.

* * * * *